(12) United States Patent
Hwang et al.

(10) Patent No.: US 8,107,059 B2
(45) Date of Patent: Jan. 31, 2012

(54) NON-INVASIVE PROBE FOR MEASURING BODY COMPONENTS AND A NON-INVASIVE BODY COMPONENT MEASUREMENT SYSTEM INCLUDING THE NON-INVASIVE PROBE

(75) Inventors: In-duk Hwang, Suwon-si (KR);
Kun-kook Park, Suwon-si (KR);
Hong-sig Kim, Seongnam-si (KR);
Soo-kwan Kim, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 355 days.

(21) Appl. No.: 11/950,629

(22) Filed: Dec. 5, 2007

(65) Prior Publication Data
US 2009/0051898 A1 Feb. 26, 2009

(30) Foreign Application Priority Data

Aug. 24, 2007 (KR) ........................ 10-2007-0085563

(51) Int. Cl.
*G01N 33/48* (2006.01)
(52) U.S. Cl. ........... 356/39; 600/341; 600/324; 600/476
(58) Field of Classification Search .................... 356/39; 600/365, 473
See application file for complete search history.

(56) References Cited

U.S. PATENT DOCUMENTS

| 5,615,673 | A  | * | 4/1997 | Berger et al. ................. 600/326 |
| 6,353,471 | B1 | * | 3/2002 | Samsoondar et al. .......... 356/40 |
| 7,623,233 | B2 | * | 11/2009 | Freese et al. .................. 356/303 |
| 2002/0151774 | A1 | * | 10/2002 | Soller et al. .................... 600/318 |
| 2007/0179366 | A1 | * | 8/2007 | Pewzner et al. ............... 600/310 |
| 2007/0203403 | A1 | * | 8/2007 | Rubinstein et al. ........... 600/309 |
| 2009/0002697 | A1 | * | 1/2009 | Freese et al. .................. 356/300 |
| 2009/0015819 | A1 | * | 1/2009 | Van Beek et al. .............. 356/39 |
| 2009/0219539 | A1 | * | 9/2009 | Myrick et al. ................. 356/445 |

* cited by examiner

*Primary Examiner* — Tarifur Chowdhury
*Assistant Examiner* — Isiaka Akanbi
(74) *Attorney, Agent, or Firm* — Sughrue Mion, PLLC

(57) ABSTRACT

A non-invasive probe for measuring body components, and a non-invasive body component measurement system including the non-invasive probe is provided. The non-invasive probe includes an input light transferring unit for transferring an input light emitted from a light source; a light splitting unit for splitting the input light into a plurality of living body incident lights; a light condensing unit for condensing the plurality of living body incident lights, so that the plurality of living body incident lights can be irradiated onto a plurality of measuring points, each measuring point corresponding to one of the plurality of living body incident lights; and an output light transferring unit for transferring a plurality of output lights, which each correspond to the one of the plurality of measuring points and, which are obtained by irradiating the plurality of living body incident lights, to a spectrometer that classifies the output lights by wavelength.

17 Claims, 4 Drawing Sheets

NON-INVASIVE PROBE FOR MEASURING BODY COMPONENTS AND A NON-INVASIVE BODY COMPONENT MEASUREMENT SYSTEM INCLUDING THE NON-INVASIVE PROBE

CROSS REFERENCE TO RELATED PATENT APPLICATION

This application claims priority from Korean Patent Application No. 10-2007-0085563, filed on Aug. 24, 2007, in the Korean Intellectual Property Office, the disclosure of which is incorporated herein in its entirety by reference.

BACKGROUND OF THE INVENTION

1. Field of the Invention

Apparatuses consistent with the present invention relate to a non-invasive measurement of body components and, more particularly, to a system for non-invasively measuring body components using Raman spectroscopy and a non-invasive probe included in the system.

2. Description of the Related Art

As the quality and environment of life have been greatly improved, peoples' interest in individual health has increased. Thus, research for developing household medical instruments, by which a person's state of health can be easily checked, has been performed, and a lot of new products are being developed. In the body of a normal person, bio-fluids exist, which are organically circulated and controlled to be maintained within a predetermined range. The bio-fluids can include blood, urine, interstitial fluid, and sweat. Concentrations of bio-fluid components such as glucose, hemoglobin, bilirubin, cholesterol, albumin, creatinine, protein, and urea included in the bio-fluid are among the variables which represent the state of a person's health, and thus are among the subjects to be measured.

If a person suffers from an illness, the composition or quantity of the bio-fluid components changes, and that person can be in danger. For example, the concentration of blood glucose of a normal person is about 80 mg/dl before a meal, and about 120 mg/dl after a meal. The human body makes the pancreas produce an appropriate amount of insulin before or after the meal and the liver and skeletal muscle cells absorb the insulin in order to maintain the above concentration of the blood glucose.

However, if the appropriate amount of insulin required to maintain the normal blood glucose cannot be produced by the pancreas due to an illness or other cause, an excessive amount of glucose will exist in the blood, which may cause heart disease, liver disease, arteriosclerosis, hypertension, cataract, retinal hemorrhage, nerve damage, loss of hearing ability, amblyopia, or even worse, the person's death. Therefore, it is very important to diagnose a person's state of health by measuring the concentrations of the bio-fluid components before any illnesses result.

The concentration of the bio-fluid components, in particular, the blood glucose included in blood, can be measured by using an invasive method, which measures the concentration of a certain bio-fluid component by directly collecting blood. Alternatively, a non-invasive method, which measures the concentration of the bio-fluid component without collecting the blood can be used. While the invasive method can obtain highly reliable measurements, it also has several disadvantages including the pain caused by the blood collection using a syringe, possible infection and inconvenience. In addition, direct blood collection imposes an economic burden on a user due to the need for supplies such as a strip for measuring the bio-fluid component and the syringe.

Non-Invasive Technique for measuring the bio-fluid components, such as the blood glucose, using Raman spectroscopy are well known. According to these Techniques a ray of light having a certain wavelength is focused and irradiated onto a certain portion of the body, a capillary vessel for example, and the concentration of blood glucose is measured using a Raman spectrum, the wavelength of which is changed by glucose molecules.

According to the measuring method using Raman spectroscopy, the magnitude of signals in a Raman spectrum, which is obtained by irradiating the light, is small. To solve this problem, the intensity of the light incident into the human body can be increased; However, the increased intensity of light may cause a burn. Alternatively, the concentration of blood glucose can be measured using a plurality of Raman spectrum signals obtained by irradiating the light multiple times; however, it may take three minutes or longer to measure the concentration of the blood glucose using multiple irradiations of light.

SUMMARY OF THE INVENTION

An Apparatus consistent with the present invention may provide a non-invasive probe for measuring body components, in which a plurality of Raman spectrums may be obtained by irradiating rays of light onto a plurality of measuring points. A non-invasive body component measurement system including the probe may also be provided.

According to one aspect of the present invention, there is provided a non-invasive probe for measuring body components, the probe including: an input light transferring unit, which transfers an input light emitted from a light source; a light splitting unit, which splits the input light into a plurality of living body incident lights; a light condensing unit, which condenses the plurality of living body incident lights so that the plurality of living body incident lights can be irradiated onto measuring points corresponding to the living body incident lights; and an output light transferring unit which transfers a plurality of output lights, which correspond to the number of the measuring points and are obtained by irradiating the plurality of living body incident lights, to a spectrometer that classifies the output lights by a wavelength unit.

According to second aspect of the present invention, there is provided a non-invasive body component measurement system, the system including: a light source, which emits an input light; a non-invasive probe, which irradiates the input light onto a plurality of measuring points of a living body to obtain a plurality of output lights that correspond to the number of the measuring points; a spectrometer, which classifies the plurality of output lights by a wavelength unit; a photo sensing array which senses the plurality of output lights that are classified by wavelength and which generates electric signals corresponding to the output lights; and a processor, which measures a concentration of a body component by processing the electric signals The probe may further include a light filtering unit, which filters light components, which have the same wavelength bands as the input light, from the plurality of output lights.

The light filtering unit may include a plurality of notch filters, each notch filter corresponding to one of the plurality of output lights.

The input light transferring unit may include an optical fiber core.

The output light transferring unit may include a plurality of optical fiber cores, each optical fiber core corresponding to one of the plurality of output lights.

The light condensing unit may include a plurality of objective lenses, each objective lens corresponding to one of the plurality of living body incident lights.

The light splitting unit may split the input light into two living body incident lights.

The light splitting unit may include a beam splitter having an input light incident surface that reflects a portion of the input light and transmits an unreflected portion of the input light.

The beam splitter may further include an output light reflecting surface that reflects the output lights on an opposite surface of the input light incident surface.

The probe may further include: a selective transmission mirror that reflects one of the two living body incident lights, and transmits the output lights.

The light source may include a laser diode (LD), which emits near-infrared light.

The LD may emit light having a maximum intensity at a wavelength of 785 nm.

The spectrometer may include a wavelength spectro-device.

The wavelength spectro-device may be a diffraction grating.

The photo sensing array may include a plurality of pixels, which senses the light, and the pixels may be classified as a plurality of pixel groups, each pixel group corresponding to one of the plurality of output lights.

According to one aspect of the present invention, a plurality of Raman spectrums may be obtained by irradiating the lights onto a plurality of measuring points, and thus, the light intensity irradiated to measure the body components may be maintained at a harmless level. In addition, a reliable measuring result may be obtained within a short period of time.

In addition, if the lights are irradiated simultaneously to the plurality of measuring points under different conditions such as the temperature or the pressure, the reliable result may be obtained through a tissue modulation.

Some illustrative embodiments of the present invention may allow more reliable measurements within a shorter time or may allow reliable results to be obtained through tissue modulation. However, an embodiment is not required to allow for more reliable results to be obtained.

BRIEF DESCRIPTION OF THE DRAWINGS

Aspects of the present invention will become more apparent by describing in detail exemplary embodiments thereof with reference to the attached drawings in which.

DETAILED DESCRIPTION OF THE INVENTION

Hereinafter, a non-invasive probe for measuring body components and a non-invasive body component measurement system including the non-invasive probe according to illustrative embodiments of the present invention will be described with reference to the accompanying drawings.

Figure 1:
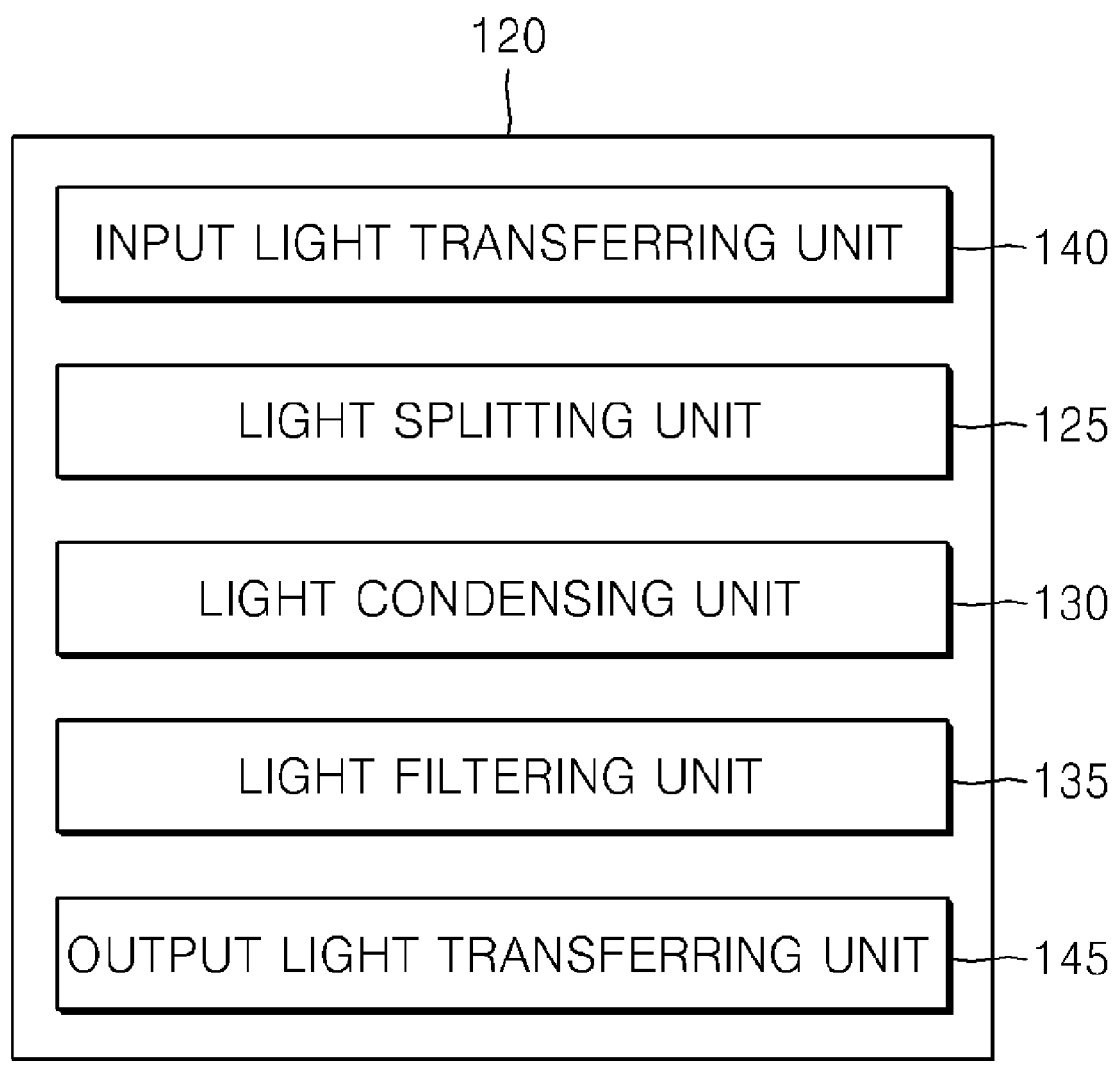
FIG. 1 is a block diagram of a non-invasive probe for measuring body components according to an exemplary embodiment of the present invention.
Figure 2:
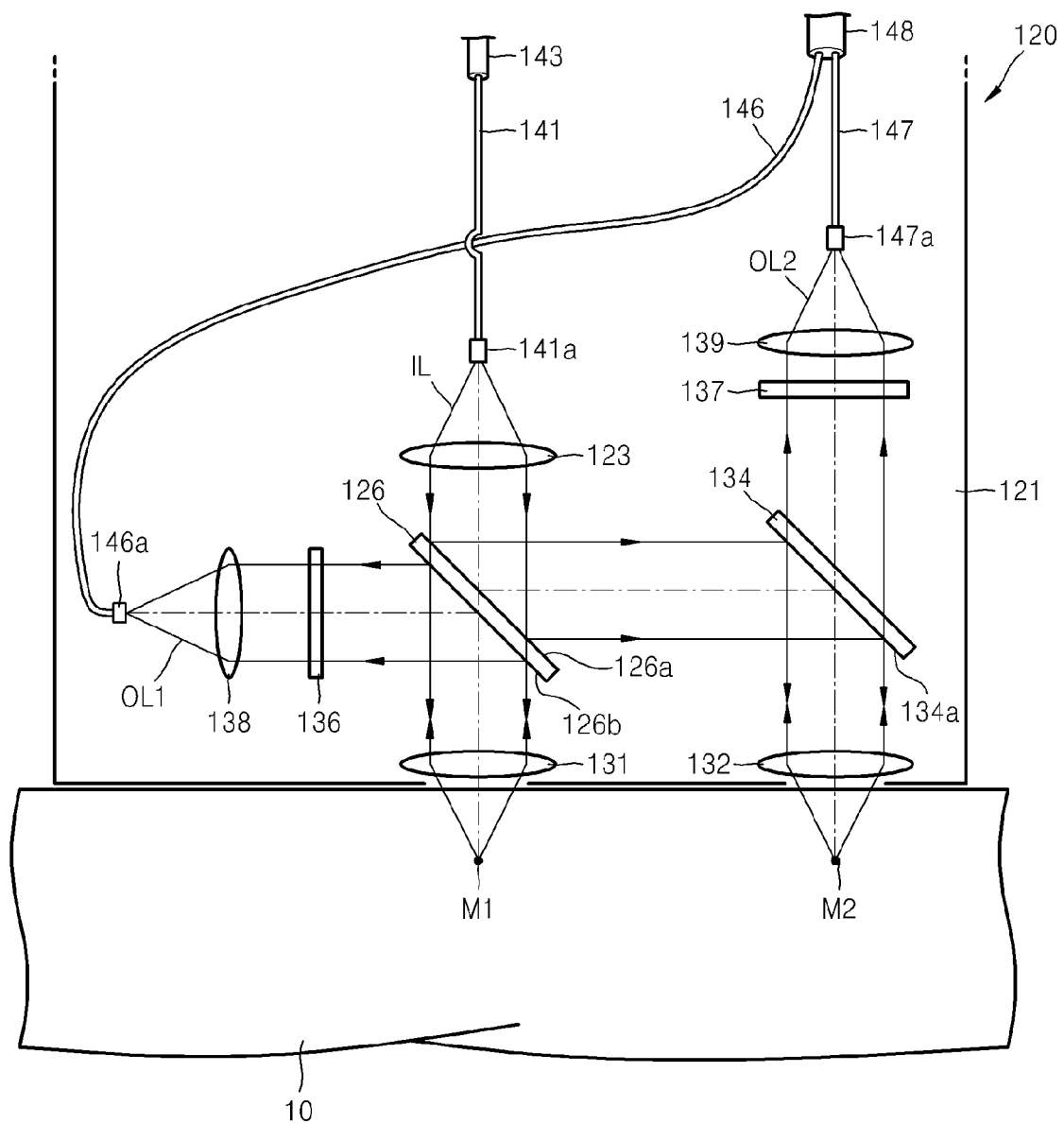
FIG. 2 is a schematic diagram of the non-invasive probe for measuring body components according to an exemplary embodiment of the present invention.
Figure 3:
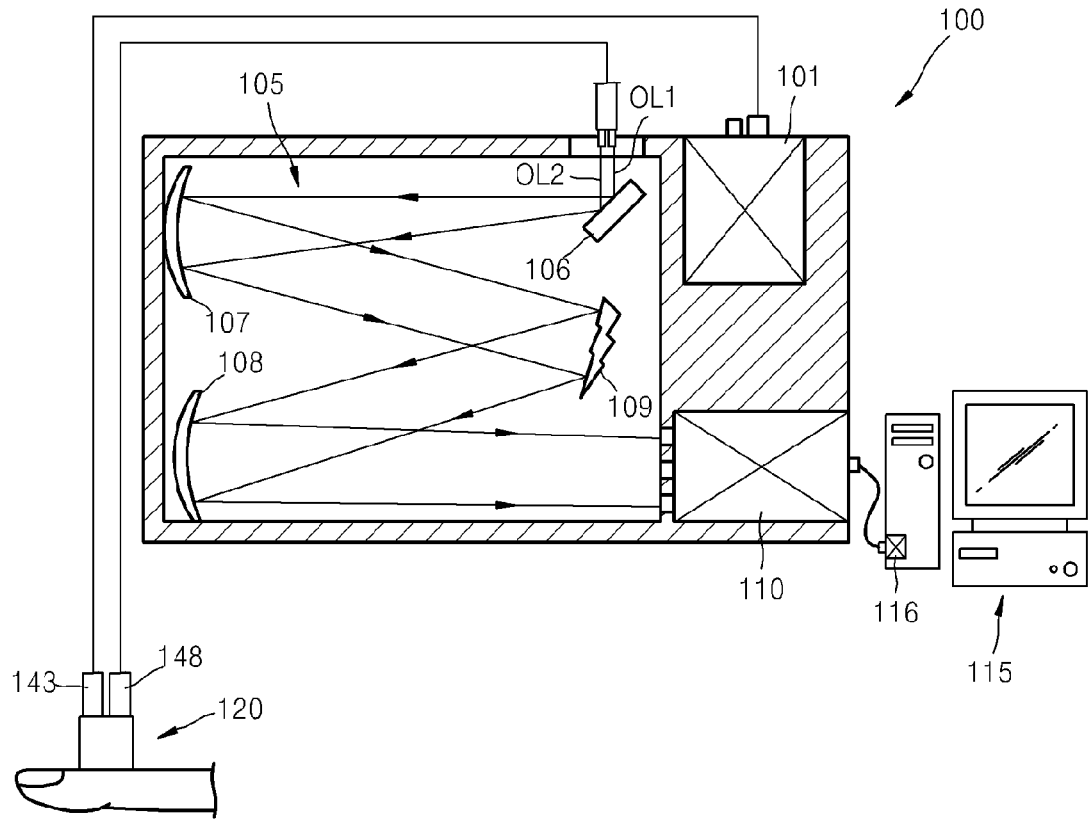
FIG. 3 is a schematic diagram of a non-invasive body component measurement system according to an exemplary embodiment of the present invention.
Figure 4:
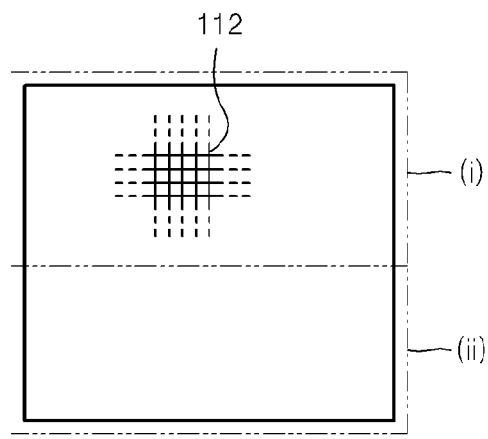
FIG. 4 is a plan view of a light incident surface of an optical sensing array shown in FIG. 3.

FIG. 1 is a block diagram of a non-invasive probe for measuring body components according to an exemplary embodiment of the present invention, FIG. 2 is a schematic diagram of the non-invasive probe for measuring body components according to an exemplary embodiment of the present invention, FIG. 3 is a schematic diagram of a non-invasive body component measurement system according to an exemplary embodiment of the present invention, and FIG. 4 is a plan view of a light incident surface of an optical sensing array shown in FIG. 3.

Referring to FIG. 3, the non-invasive body component measurement system 100 according to an exemplary embodiment of the present invention includes a light source 101 for emitting an input light (IL, refer to FIG. 2), a non-invasive probe 120 (hereinafter, referred to as probe) for irradiating the input light IL onto a plurality of measuring points M1 and M2 (refer to FIG. 2) of a living body 10 to obtain a plurality of output lights OL1 and OL2, each output light corresponding to one of the plurality of measuring points, a spectrometer 105 for classifying the plurality of output lights OL1 and OL2 by a wavelength unit, a photo sensing array 110 for sensing the plurality of output lights OL1 and OL2 that are classified by wavelength and for generating electric signals which correspond to the output lights OL1 and OL2, and a processor 116 for processing the electric signals to measure the concentration of body components.

In more detail, the body component measurement system 100 may measure the component concentration of a bio-fluid, such as blood glucose using Raman spectroscopy. The light source 101 can include a laser diode (LD) emitting near-infrared rays in order to obtain a plurality of Raman spectrums that are suitable for measuring the concentration of blood glucose from the output lights OL1 and OL2. The LD may be a LD, which emits light having a maximum intensity at a wavelength of 785 nm. The LD is suitable for the Raman spectroscopy because the light emitted from the LD has a bandwidth that is narrower than that emitted from other light emitting devices, such as LED.

Referring to FIGS. 1 and 2, the probe 120 includes an input light transferring unit 140 transferring the input light IL emitted from the light source 101 (refer to FIG. 3), a light splitting unit 125 splitting the input light IL that passes through the input light transferring unit 140 into a plurality of living body incident lights, which each correspond to one of the plurality of measuring points M1 and M2, a light condensing unit 130 for concentrating each of the plurality of living body incident lights so that each of the plurality of living body incident lights can be irradiated onto one of the plurality of measuring points M1 and M2, and an output light transferring unit 145 for transferring the plurality of output lights OL1 and OL2, which each correspond to one of the plurality of measuring points M1 and M2 and which are obtained by irradiating the plurality of living body incident lights, to the spectrometer 105 (refer to FIG. 3). In addition, the probe 120 may further include a light filtering unit 135 for filtering the light components, which have the same wavelength as the input light IL, from the plurality of output lights OL1 and OL2.

The probe 120 shown in the drawings is a probe for obtaining two Raman spectrums by irradiating the living body incident lights onto two measuring points of the living body 10. However, the present invention can include a probe that can obtain more than two Raman spectrums. The living body 10 shown in the drawings is a finger, but this is merely an example. The probe 120 of the present invention can be applied to other parts of the human body, for example, forearms. The first measuring point M1 and the second measuring point M2 may be set on a dermis, in which a lot of capillary vessels are distributed.

The input light transferring unit 140 includes an input light cable 143 having one optical fiber core 141 so as to transfer one ray of input light IL. The input light cable 143 connects the light source 101 (refer to FIG. 3) to a probe housing 121. The output light transferring unit 145 includes an output light cable 148 having two optical fiber cores 146 and 147, each optical fiber core corresponding to one of the plurality of output lights OL1 and OL2. The output light cable 148 connects the probe housing 121 to the spectrometer 105 (refer to FIG. 3).

The light splitting unit 125 includes a beam splitter 126 that divides the input light IL emitted from an end 141a of the optical fiber core 141 into two living body incident lights. The beam splitter 126 includes an input light incident surface 126a that reflects a portion of the input light IL, for example, about half of the input light IL intensity, and transmits an unreflected portion other of the input light IL. The unreflected portion of input light IL becomes the first living body incident light, and the reflected portion of the input light IL becomes the second living body incident light. A collimating lens 123, which makes the input light IL output from the end 141a parallel, is disposed between the end 141a of the optical fiber core 141 and the beam splitter 126.

The light condensing unit 130 includes a plurality of objective lenses 131 and 132, each objective lens corresponding to one of the plurality of living body incident lights that are divided by the beam splitter 126. The probe 120 shown in FIG. 2 includes a pair of objective lenses 131 and 132. The first objective lens 131 condenses the first living body incident light onto the first measuring point M1, and the second objective lens 132 condenses the second living body incident light onto the second measuring point M2.

The probe 120 further includes a selective transmission mirror 134 that changes a path of the second living body incident light toward the second objective lens 132. The selective transmission mirror 134 reflects the second living body incident light, and transmits the second output light OL2 from the second measuring point M2. This characteristic of the selective transmission mirror 134 can be obtained by a material coating, which reflects the light at the same wavelength band as that of the living body incident light and which transmits the light at the same wavelength band as that of the Raman spectrum, being applied to a light incident surface 134a of the selective transmission mirror 134. The wavelength band of the living body incident light is about 785 nm, which is equal to the wavelength band of the input light IL, and the wavelength band of the Raman spectrum, which is obtained by Stokes scattering, is longer than the wavelength of the input light IL.

The first output light OL1 scattered out of the living body 10 by the first living body incident light irradiated onto the first measuring point M1 proceeds toward the first objective lens 131 in parallel, but is reflected by the beam splitter 126 to another direction. In order to reflect the first output light OL1, the beam splitter 126 includes an output light reflecting surface 126b on the surface opposite to the light incident surface 126a for reflecting the output light OL1. Meanwhile, the second output light OL2 scattered out of the living body 10 by the second living body incident light irradiated onto the second measuring point M2 proceeds toward the second objective lens 132 in parallel, and is transmitted through the selective transmission mirror 134.

In the embodiment shown in FIG. 2, the light filtering unit 135 includes two notch filters 136 and 137, each notch filter corresponding to one of the output lights OL1 and OL2. The first notch filter 136 is located in a light path of the first output light OL1, the direction of which is changed by the beam splitter 126, to absorb the light having the wavelength of about 785 nm, which is the same wavelength as the input light IL. The second notch filter 137 is located in a light path of the second output light OL2 that transmits through the selective transmission mirror 134 to absorb the light having the wavelength band of about 785 nm, which is the same wavelength band as the input light IL.

The probe 120 further includes a first output light condensing lens 138, which condenses the first output light OL1 transmitted through the first notch filter 136 onto an end 146a of the optical fiber core 146, and a second output light condensing lens 139, which condenses the second output light OL2 transmitted through the second notch filter 137 onto an end 147a of the optical fiber core 147.

The first and second output lights OL1 and OL2, from which the optical components of the input light IL are removed by the first and second notch filters 136 and 137, are transferred to the spectrometer 105 through the optical fiber cores 146 and 147, respectively.

Referring to FIG. 3, the spectrometer 105 includes mirrors 106, 107, and 108 for changing the light paths of the first and second output lights OL1 and OL2, and a wavelength spectro-device 109 disposed in the light paths of the output lights OL1 and OL2. In one embodiment of the present invention, the wavelength spectro-device 109 can be a diffraction grating. The first and second output lights OL1 and OL2 are divided along light paths that are appropriately separated from each other, so as not to interfere with each other, and transmitted incident upon the photo sensing array 110.

According to one embodiment of the present invention, the photo sensing array 110 can be a charge coupled device (CCD) array. Referring to FIG. 4, a light incident surface of the photo sensing array 110 includes a plurality of pixels 112 for sensing the light. The plurality of pixels 112 are classified into a plurality of pixel groups, each pixel group corresponding to one of the plurality of output lights. In this embodiment, the pixels 112 are divided into two pixel groups i and ii to correspond to the two output lights OL1 and OL2. The first output light OL1 is sensed by the pixels 112 in the first pixel group i and classified by wavelength, and the second output light OL2 is sensed by the pixels 112 in the second pixel group ii and classified by wavelength.

The photo sensing array 110 is electrically connected to a host computer 115, and a processor 116 in the host computer 115 analyzes the electric signals, which correspond to the spectrums of the output lights OL1 and OL2, input from the photo sensing array 110, to measure the concentration of a body component, like blood glucose, for example.

Figure 5A:
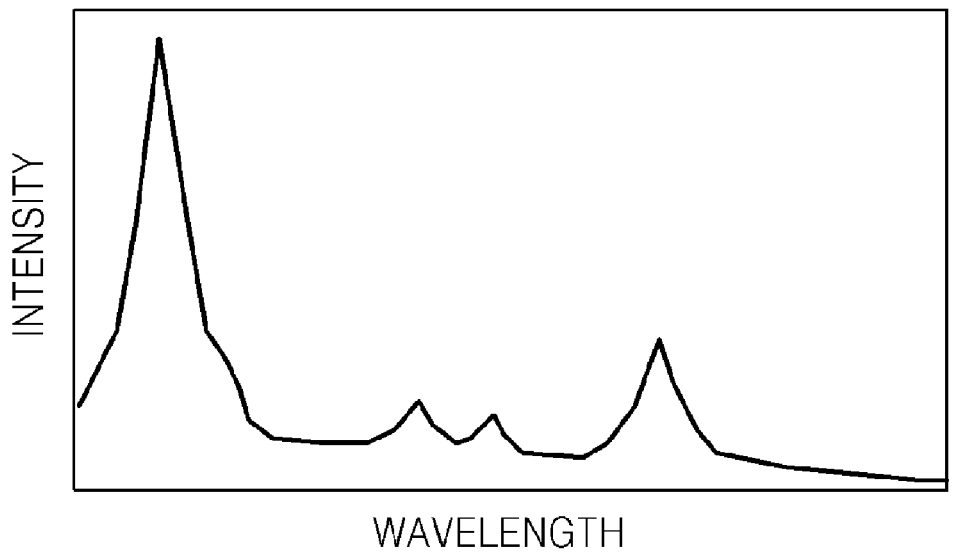
FIG. 5A is a graph showing an example of a Raman spectrum that may be obtained by irradiating a laser onto a first measuring point of FIG. 2.
Figure 5B:
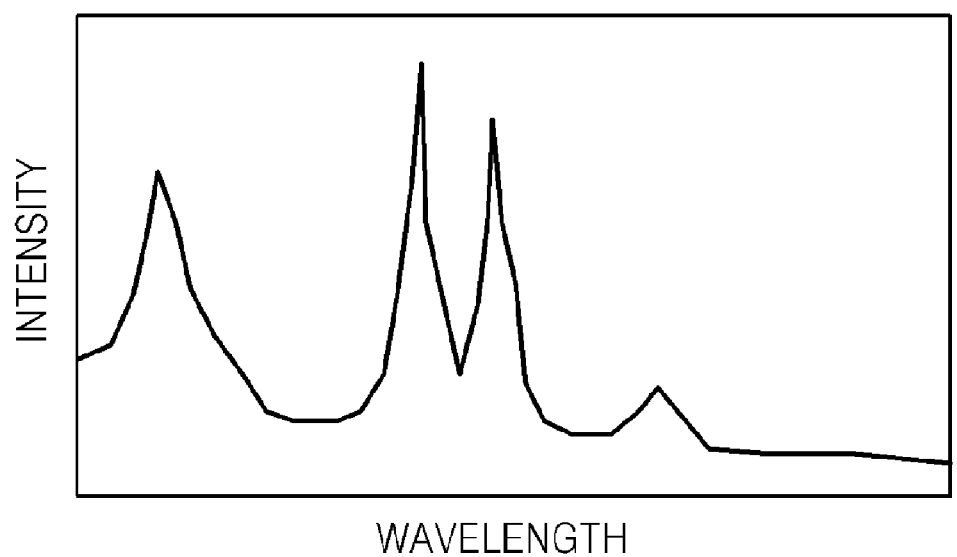
FIG. 5B is a graph showing an example of a Raman spectrum that may be obtained by irradiating a laser onto a second measuring point of FIG. 2.

FIG. 5A is a graph showing an example of a Raman spectrum obtained by irradiating a laser onto the first measuring point of FIG. 2, and FIG. 5B is a graph showing an example of a Raman spectrum obtained by irradiating a laser onto the second measuring point of FIG. 2.

The electric signals obtained by converting the light sensed by the first pixel group i of the photo sensing array 110 are processed by the processor 116 to obtain the Raman spectrum shown in FIG. 5A, and the electric signals obtained by converting the light sensed by the second pixel group ii are processed by the processor 116 to obtain the Raman spectrum shown in FIG. 5B.

The processor 116 processes the plurality of Raman spectrums to measure the concentration of a body component, for example, the blood glucose. The concentration of the body components can be measured in various ways. For example, a spectrum can be obtained by summing up the plurality of Raman spectrums, or a spectrum can be obtained by summing up the plurality of Raman spectrums, but omitting any Raman spectrum determined to be an error. Otherwise, a plurality of Raman spectrums may be obtained by changing conditions such as temperature or pressure with respect to the plurality of measuring points, and then, the concentration of the body component can be measured using a differential spectrum between the plurality of Raman spectrums.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A non-invasive probe for measuring body components, the probe comprising:
    a single probe housing;
    an input light transferring unit, which transfers an input light emitted from a light source;
    a light splitting unit, which splits the input light into a plurality of incident lights;
    a light condensing unit, which condenses the plurality of incident lights so that each of the plurality of the incident lights can be irradiated onto one of a plurality of measuring points, each measuring point corresponding to one of the plurality of incident lights; and
    an output light transferring unit, which transfers a plurality of output lights, which each correspond to one of the plurality of measuring points and which are obtained by irradiating the plurality of incident lights, to a spectrometer that classifies the output lights by wavelength;
    wherein each of the light splitting unit and the light condensing unit are disposed within the single probe housing, and the light splitting unit includes a beam splitter having an input light incident surface that reflects a portion of the input light as a first incident light of the plurality of incident lights and transmits an unreflected portion of the input light as a second incident light of the plurality of incident lights, and an output light reflecting surface opposite to the input light incident surface which reflects the output lights, and the probe further comprises a selective transmission mirror that reflects the second incident light and transmits the output lights.

2. The probe of claim 1, further comprising:
    a light filtering unit, which filters light components, which having the same wavelength as the input light, from the plurality of output lights.

3. The probe of claim 2, wherein the light filtering unit includes a plurality of notch filters, each of the notch filters corresponding to one of the plurality of output lights.

4. The probe of claim 1, wherein the input light transferring unit includes an optical fiber core.

5. The probe of claim 1, wherein the output light transferring unit includes a plurality of optical fiber cores, each of optical fiber cores corresponding to one of the plurality of output lights.

6. The probe of claim 1, wherein the light condensing unit includes a plurality of objective lenses, each of the objective lenses corresponding to one of the plurality of incident lights.

7. A non-invasive body component measurement system, the system comprising:
    a light source, which emits an input light;
    a non-invasive probe, which irradiates the input light onto a plurality of measuring points of a living body to obtain a plurality of output lights, each of the output lights corresponding to one of the plurality of measuring points;
    a spectrometer, which classifies the plurality of output lights by wavelength;
    a photo sensing array, which senses the plurality of output lights that are classified by wavelength and generates electric signals corresponding to the output lights; and
    a processor, which measures a concentration of a body component by processing the electric signals,
    wherein the non-invasive probe comprises:
    a single probe housing;
    an input light transferring unit, which transfers the input light;
    a light splitting unit, which splits the input light into a plurality of incident lights, each of the incident lights corresponding to one of the plurality of measuring points;
    a light condensing unit, which condenses the plurality of incident lights so that each of the plurality of incident lights can be irradiated onto one of the plurality of measuring points; and
    an output light transferring unit, which transfers a plurality of output lights, which each correspond to one of the plurality of measuring points and, which are obtained by irradiating the plurality of incident lights, to the spectrometer;
    wherein each of the light splitting unit and the light condensing unit are disposed within the single probe housing, and the light splitting unit includes a beam splitter having an input light incident surface that reflects a portion of the input light as a first incident light of the plurality of incident lights and transmits an unreflected portion of the input light as a second incident light of the plurality of incident lights, and an output light reflecting surface opposite to the input light incident surface, which reflects the output lights, and the probe further comprises a selective transmission mirror that reflects the second incident light and transmits the output lights.

8. The system of claim 7, wherein the non-invasive probe further includes a light filtering unit, which filters light components, which have the same wavelength bands as the input light, from the plurality of output lights.

9. The system of claim 8, wherein the light filtering unit includes a plurality of notch filters, each of the notch filters corresponding to one of the plurality of output lights.

10. The system of claim 7, wherein the input light transferring unit includes an optical fiber core.

11. The system of claim 7, wherein the output light transferring unit includes a plurality of optical fiber cores, each of the optical fiber cores corresponding to one of the plurality of output lights.

12. The system of claim 7, wherein the light condensing unit includes a plurality of objective lenses, each of the objective lenses corresponding to one of the plurality of incident lights.

13. The system of claim 7, wherein the light source includes a laser diode (LD) which emits near-infrared lights.

14. The system of claim 13, wherein the LD emits light having a maximum intensity at a wavelength of 785 nm.

15. The system of claim 7, wherein the spectrometer includes a wavelength spectro-device.

16. The system of claim 15, wherein the wavelength spectro-device is a diffraction grating.

17. The system of claim 7, wherein the photo sensing array includes a plurality of pixels, which senses the light, and the pixels are classified as a plurality of pixel groups, each of the pixel groups corresponding to one of the plurality of output lights.

* * * * *